United States Patent

Smead

(10) Patent No.: US 9,149,681 B2
(45) Date of Patent: Oct. 6, 2015

(54) TONGUE PRESS ORAL EXERCISER

(71) Applicant: Kathleen Smead, Pensacola, FL (US)

(72) Inventor: Kathleen Smead, Pensacola, FL (US)

(*) Notice: Subject to any disclaimer, the term of this patent is extended or adjusted under 35 U.S.C. 154(b) by 193 days.

(21) Appl. No.: 13/971,809

(22) Filed: Aug. 20, 2013

(65) Prior Publication Data

US 2014/0066258 A1    Mar. 6, 2014

Related U.S. Application Data

(60) Provisional application No. 61/695,976, filed on Aug. 31, 2012.

(51) Int. Cl.
| | | |
|---|---|---|
| A63B 23/03 | (2006.01) | |
| A63B 21/02 | (2006.01) | |
| A63B 21/00 | (2006.01) | |
| A61B 5/22 | (2006.01) | |

(52) U.S. Cl.
CPC ............. A63B 23/032 (2013.01); A63B 21/02 (2013.01); A63B 21/158 (2013.01); *A61B 5/224* (2013.01); *A63B 21/00061* (2013.01); *A63B 2220/51* (2013.01)

(58) Field of Classification Search
CPC ............. A63B 23/032; A63B 21/158; A63B 21/0012; A63B 21/0081; A63B 2220/56; A61B 5/224; A61B 5/228; A61B 5/682; A61B 5/038
USPC ............................................ 482/11; 600/590
See application file for complete search history.

(56) References Cited

U.S. PATENT DOCUMENTS

| | | | | |
|---|---|---|---|---|
| 4,530,496 | A * | 7/1985 | Smith et al. ................. | 482/112 |
| 4,585,012 | A * | 4/1986 | Rumburg .................... | 600/590 |
| 4,697,601 | A * | 10/1987 | Durkee et al. .............. | 600/590 |
| 5,609,161 | A * | 3/1997 | Tura et al. ................... | 600/590 |
| 6,050,961 | A * | 4/2000 | Arnold ........................ | 600/590 |
| 6,702,765 | B2 * | 3/2004 | Robbins et al. ............. | 600/590 |
| 7,238,145 | B2 | 7/2007 | Robbins et al. | |
| 7,438,667 | B2 | 10/2008 | Robbins et al. | |
| 8,226,581 | B2 * | 7/2012 | Rampi et al. ............... | 600/590 |
| 8,366,639 | B2 * | 2/2013 | Toyota et al. ............... | 600/587 |
| 8,376,912 | B1 | 2/2013 | Dedvukaj | |
| 8,425,385 | B2 | 4/2013 | Bonutti | |
| 8,663,131 | B2 * | 3/2014 | Cunningham et al. ..... | 600/590 |
| 8,784,341 | B2 * | 7/2014 | Friedland et al. .......... | 600/590 |
| 8,905,947 | B2 * | 12/2014 | Annett et al. .............. | 600/590 |
| 2010/0222706 | A1 * | 9/2010 | Miyahara et al. .......... | 600/590 |

FOREIGN PATENT DOCUMENTS

WO   WO 2011136427 A1 *  11/2011   ............ A61C 19/04

OTHER PUBLICATIONS

Office Playground, Handheld Waer Game—Triangles, Jul. 17, 2011; http://www.officeplayground.com/Handheld-Water-Game-Triangles-P1907.aspx.*

* cited by examiner

*Primary Examiner* — Joshua Kennedy

(57) ABSTRACT

A therapeutic apparatus for strengthening the tongue. The device is a water-filled unit comprised of clear tube with two bulbs on each end. The exerciser is activated in the mouth by pressing the pressurized bulb with the tongue against the hard palate. A floating indicator in the tube offers visual feedback and elevates as the tube is compressed. The device is adjustable in difficulty. The presenting invention is simple in design and operation. It has limited moving or articulating parts, requires no customization, is non-electrical, can be operated with one hand and is inexpensive to manufacture. The Tongue Press Oral Exerciser is an affordable means of strengthening swallowing and speech intelligibility.

16 Claims, 6 Drawing Sheets

TONGUE PRESS ORAL EXERCISER

BACKGROUND OF THE INVENTION

The present invention relates in general to a swallowing and speech therapeutic device for strengthening the lingual musculature through the use of a water-filled tube with pressurized bulbs on each end. The bulb is placed in the mouth and pressed against the hard palate with the dorsum of the tongue. The compression of the pressurized bulb exercises the tongue in an upward movement as is performed by the tongue during the act of swallowing and for speaking.

Speech and swallowing disorders can result from a number of causes including: stroke, brain disease, brain injury, developmental disorders, spinal cord injury, multiple sclerosis, amyotrophic later sclerosis (ALS), muscular dystrophy, Alzheimer's disease, Huntington's disease, Parkinson's disease, cerebral palsy, autism, and cleft palate. Loss of tongue strength as a result of these etiologies can lead to swallowing disorders and impaired speech intelligibility. Head and neck cancers of the throat or mouth with or without concomitant radiation can result in impaired swallow or speech. Disorders of the swallow (dysphagia) can lead to lengthy or repetitive hospitalizations, a number of resulting illnesses such as pneumonia and a loss of the enjoyment of eating. Communication loss as a result of tongue weakness leads to dependency on others for care and emotional decline.

In addition to medical causes, tongue strength can also decline in the elderly. This age related tongue weakening can result in physical disease and reduced pleasure in eating Dysphagia treatment may involve modification of the patient's diet to foods or liquid consistencies that are easier to swallow. Swallowing therapy incorporates exercises for strengthening and coordinating the swallowing muscles and stimulating the nerves that trigger the swallow to respond. The size, strength and power of the tongue are important components to safe swallowing of liquids as well as solid food.

Dysarthria is the loss of speech clarity due to weakness of the oral musculature.

Speech pathologists use speech sound drills and motor exercises to increase the strength of the tongue as well as the lips and palate. More specifically, exercises to increase the strength of the tongue, the range of movement and the speed of tongue movement are a large focus in this type of care.

Equipment and devices are available to exercise the tongue in the therapy setting but very few are available for patients to purchase for home exercise. An example of a tongue exercise clinical tool is the Iowa Oral Proficiency Instrument (IOPI), which is described in the article, *Swallowing and Tongue Function Following Treatment For Oral and Oropharyngeal Cancer*, by Lazarus, et al. 2000, Journal of Speech, Language and Hearing Research 43, 1011. The IOPI uses an air-filled bulb, which is connected by a hose to a manometer instrument. The free moving small balloon is placed on the patient's tongue and pressed by the patient against the hard palate. The instrument provides a digital quantitative score of tongue strength in kilopascals. It has a light display that can be set manually to a desired level and lights up as the air-pressured bulb is pressed. This light acts as visual feedback to motivate the patient to press with greater effort. The IOPI can be used to diagnostically measure tongue strength and to exercise the tongue but due to its cost it can only be used in direct care. Research has clearly supported the use of this device with such populations as the elderly who often experience age related tongue weakness leading to increased difficulty eating or drinking.

A similar oral exercise system used for swallowing and speech rehabilitation was described by Hewitt et al. in the article, *Standardized Instrument for Lingual Pressure Measure*, 2008, Dysphagia 23: 16-25. This tool is the Madison Oral Strengthening Therapeutic device (MOST). As presented, this device has a multi-sensor custom molded mouthpiece, which is connected to an electronic annunciator. The custom molded mouthpiece is placed in the patient's mouth and measures contact pressures between the tongue and the hard palate. As with the IOPI, MOST's cost preclude purchase or use by patients outside of research and direct care.

U.S. Pat. No. 6,050,961 reveals a system designed to address tongue weakness in the treatment of dysarthria and dysphagia. This tool utilizes a pair of planks and a pneumatic bulb positioned between the planks. The bulb is coupled to a meter that displays the strength and the duration of the force applied to the pneumatic bulb by the patient's tongue. Although this system provides feedback to the user, it is relatively complex, expensive, of limited durability as the bulb weakens or punctures and is not suited for regular use by the patient as part of an exercise regime.

The National Institutes of Health described a device to measure tongue strength termed the APLSILT. This instrument used a disposable tongue depressor mounted on a load cell held by a mechanism on an adjustable table. Only the tongue depressor was placed within the patient's mouth with the remaining portions of the mechanism being outside of the patient's mouth and supported by the table. This tool's availability is unknown but the complexity of this load cell device precludes its home use.

Robbins et al. U.S. Pat. Nos. 7,238,145 and 7,438,667 B2 describes an oral-lever resistance exercise device, which was portable and simple in design. The device patented consists of two levers that fit in the mouth and are connected by a spring or pin joint. During exercise, the user compresses the levers between the tongue and hard palate. Springs or circular rubber belts similar to O-rings provide adjustable resistance but the hard palate adaptor must be custom-molded.

U.S. Pat. No. 8,376,912 B1 by Dedvukaj 2013 describes a facial muscle exercise ball-like device and method for toning the facial and/or jaw muscles. The device is placed in the mouth and held in place by the teeth. The resistance afforded by this device is available in various psi strengths. The resistance portion of the device is outside of the mouth. This device is designed for the face and the jaw. Swallowing with the mouth open is not recommended and strengthening of the tongue is not the goal with this device. Although affordable, there does not appear to be any feedback mechanism with this tool.

Methods or systems of providing resistance exercise vary. U.S. Pat. No. 8,425,385 B2 Resistance Therapy describes utilizing fluid contained bladders that communicate with each other so that compression of one bladder causes the fluid to be transferred to a neighboring bladder. This system is adjustable to provide different workout levels and uses both bladders for working complementary muscle groups. Resistance could be adjusted by the thickness of the bladder, by valve, by size of the bladders and by viscosity of the fluids. However, this system does not use indicators, graduations, or any feedback mechanism. Nor does this method use floating devices to increase or decrease the resistance of the exercise by increasing the weight or length of items in the fluid within the bladders.

The present invention, Tongue Press Oral Exerciser was developed out of response to a need for an affordable tool for speech therapy patients to use at home. Equally as important, the device was designed to provide an exercise that would compliment the goals of care and subsequently increase the speed of recovery. As important as affordability, the device was purposely constructed to be simple to operate by patients of all levels of ability. The exerciser was developed to be capable of providing visual feedback, varying levels of difficulty, specificity of activity and isotonic/isokinetic exercise. Lastly, the present invention was engineered to be easily manufactured to insure commercial availability to patients in need of improved swallowing and speech.

SUMMARY OF INVENTION

In accordance with the present invention, the Tongue Press Oral Exerciser is an affordable, portable, simple to operate, water driven exerciser that uses adjustable resistance and visual feedback to encourage patient use outside of therapy.

The exerciser comes in different designs including a single tube version as well as the L-shaped tool with a control valve. The single tube design uses one clear tube with a buoyant vial indicator inside of it. Hollow core plugs are inserted into each end of tube to allow for the water displacement and yet keep the indicator within the tube. Silicone bulbs are attached to each end. The device operates by filling the unit with water and securing the bulbs. One bulb is placed in the mouth on the dorsum of the tongue. When the tongue presses the bulb against the hard palate the water in the unit is displaced and the indicator moves in relation to the amount of force used. The bulb on the opposing end of the exerciser expands with the movement of the water until the tongue relaxes. The indicator moves to graduations and numbers printed on the end of the tube and the user can see the amount of force they were able to generate.

This unit can be manufactured in sets of three that offer three levels of difficulty or resistance. This is accomplished by the use of buoyant indicators of three different weights. It can also be made with longer tubes and with indicators of three different lengths to increase the difficulty of the exercise as the patient improves in strength.

One advantage of the single tube design is that it may be a safer device to use with younger or less compliant patients because it has less removable small parts.

The L-shaped model of the Tongue Press Oral Exerciser works the same as the above design but it comes with a plastic adjustable control valve. On the L-shaped exerciser, the bulb on the horizontal tube is referred to as the "tongue bulb" and the one on the vertical tube is the "expansion bulb". Before use, the unit is filled with water and the bulbs are secured. The patient places the tongue bulb on his or her tongue and presses the tongue bulb against the roof of the mouth. The pressing of the bulb displaces the water in the device and moves the colored buoyant indicator in the vertical tube upward. Printed graduations on the top of the vertical tube act as feedback by allowing the patient to see the amount of pressure they exerted. Adjusting the control valve on the exerciser can make the exercise more or less challenging.

Due to the ease of operating either of the designs of the Tongue Press Oral Exerciser, it can be used with patients who have limited understanding or confusion. The simplicity of the design limits manufacturing costs making the Tongue Press Oral Exerciser an affordable adjunct to treatment.

BRIEF DESCRIPTION OF THE DRAWINGS

A more complete understanding of the present invention, and the attendant advantages and features thereof, will be readily understood by reference to the following detailed description when considered in conjunction with the accompanying drawings wherein.

DETAILED DESCRIPTION OF THE INVENTION

The present invention provides an oral exercise apparatus for strengthening the muscles used for swallowing and speech. The single tube tongue exercise unit can be a stand-alone device or alternatively may be incorporated into another design, the L-shaped unit. Both units use water to be activated, employ adjustable resistance and have visual feedback to improve patient motivation and effort.

Figure 1:
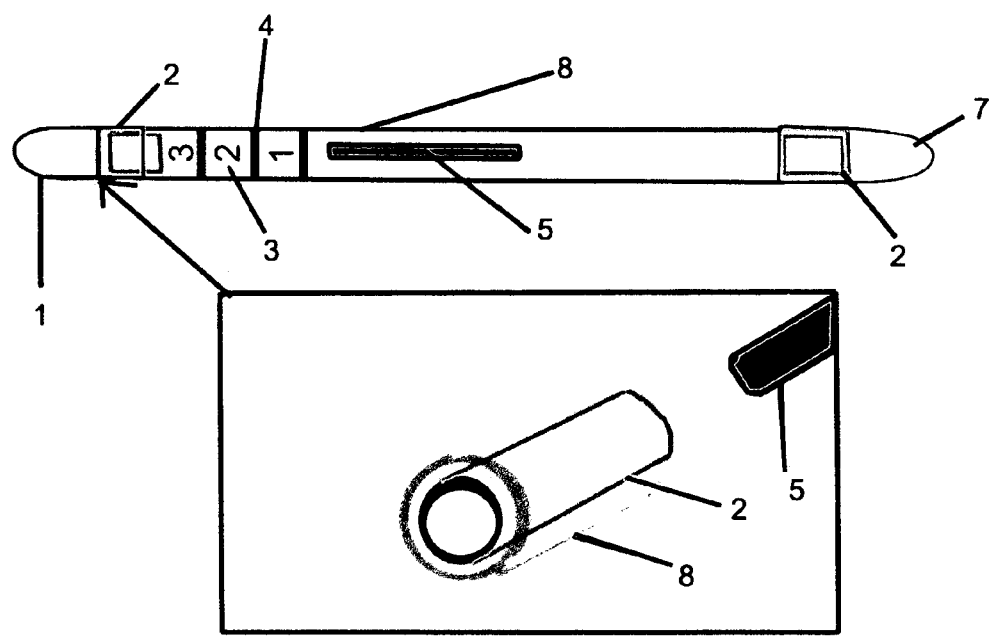
FIG. 1 depicts the single tube tongue exerciser of the present invention.
Figure 2:
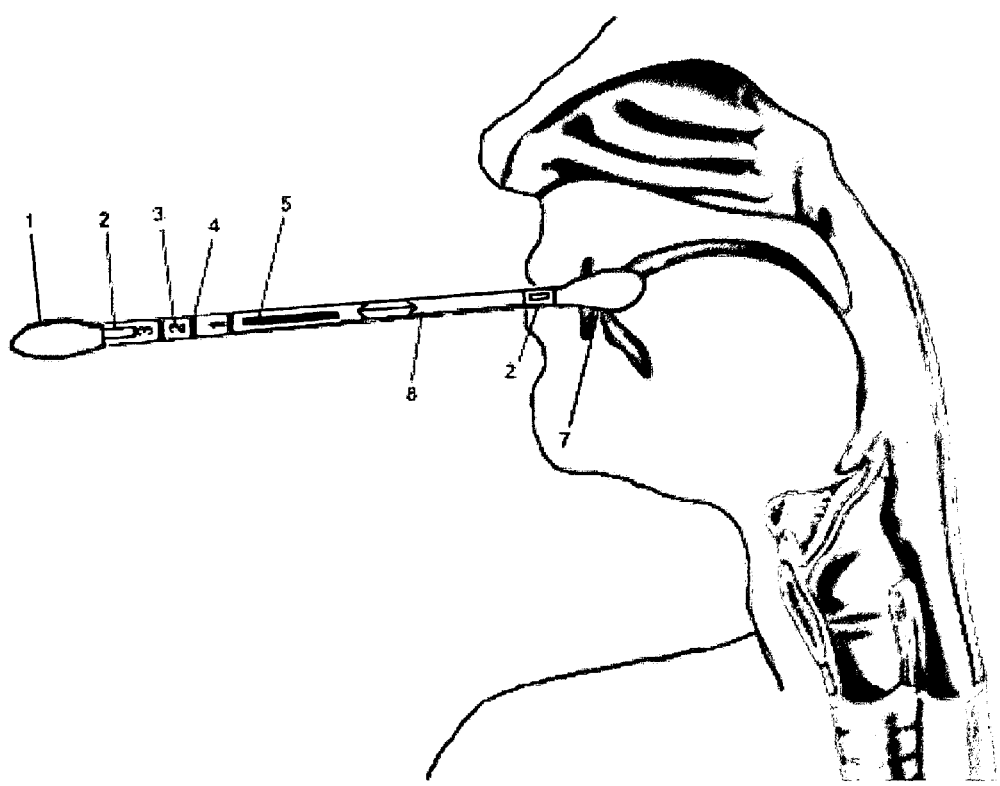
FIG. 2 depicts single tube tongue exerciser in position for use.

Referring now to the drawing in figure, FIG. 1, is illustrated one embodiment of the exercise unit, the single tube oral exerciser. This unit has a single tube 8 with the vial indicator 5 inside and two hollow core plugs 2 that are secured within each end of the tube 8 letting water move to and from the bulbs 1 and 7 but not allowing the vial indicator 5 from leaving the tube 8. The close up view in FIG. 1 shows how the hollow core plugs 2 are in the secured position. On each end of the tube 8 are 1-2 mL silicone bulbs 1 and 7. There are graduations 4 and numbers 3 on one end of the tube 8. The bulb 1 that is adjacent to the graduations 4 is the expansion bulb 1. The bulb on the opposing end of the tube 8 is the tongue bulb 7. Before the exerciser is used, the bulb 1 is removed and the tube 8 is positioned under running water. The tongue bulb 7 is lightly squeezed to help suction the water into the unit. Once the tongue bulb 7 and the tube 8 are completely filled, water is added to the expansion bulb 1 and it is securely re-attached to the device. FIG. 2 shows the tongue exerciser is position for use. The patient places the tongue bulb 7 on his or her tongue and presses it against the hard palate. The force of the tongue pressing against the bulb 7 displaces the water in the unit causing the buoyant colored indicator 5 to move laterally toward the opposing end. The indicator 5 moves to various levels marked by the graduations 4 and the numbers 3. These graduations 4 are used for visual feedback regarding the quality of the patient's effort but are not calibrated for use as a measurement, a gauge or a diagnostic score. The patient is asked to practice pressing the bulb 7, repetitively 30× or an amount specified by the clinician.

Figure 3:
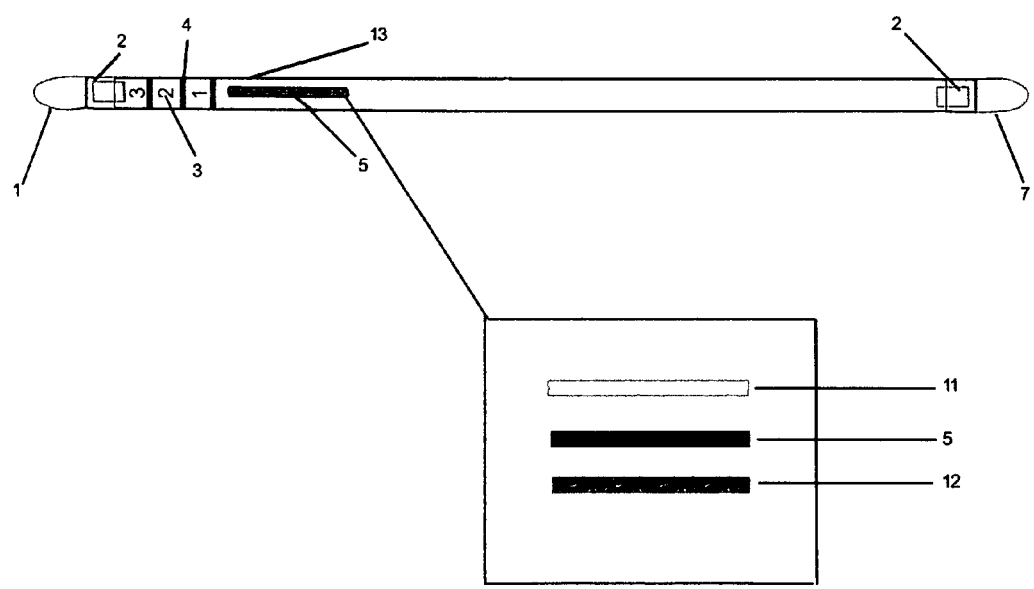
FIG. 3 depicts the single tube tongue exercise with three buoyant vial indicators of three different weights.
Figure 4:
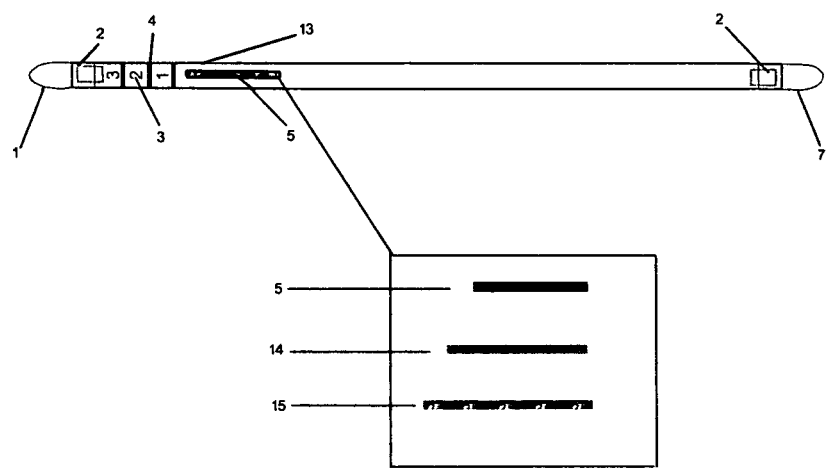
FIG. 4 depicts the single tube tongue exerciser with three buoyant vial indicators of three different lengths.

The single tube exerciser has few removable parts, which makes the device less costly to manufacture, simple to learn and safer for patients who are either non-compliant or young. To allow for adjustable resistance, FIG. 3 shows that the unit comes in a longer tube 13 version with three vial indicators 11, 5 and 12, in three various weights and colors. Additionally, FIG. 4 shows the longer tube 13 with three vial indicators 5, 14 and 15 of different lengths and colors. The modification in length of the tube 13, the various weighted vial indicators 11, 5 and 12, and the various lengths in the vial indicators 5, 14 and 15 allows the exercise unit to have adjustable levels of resistance and a design which may be appropriate to different needs of patients served. These can be packaged in sets.

Figure 5:
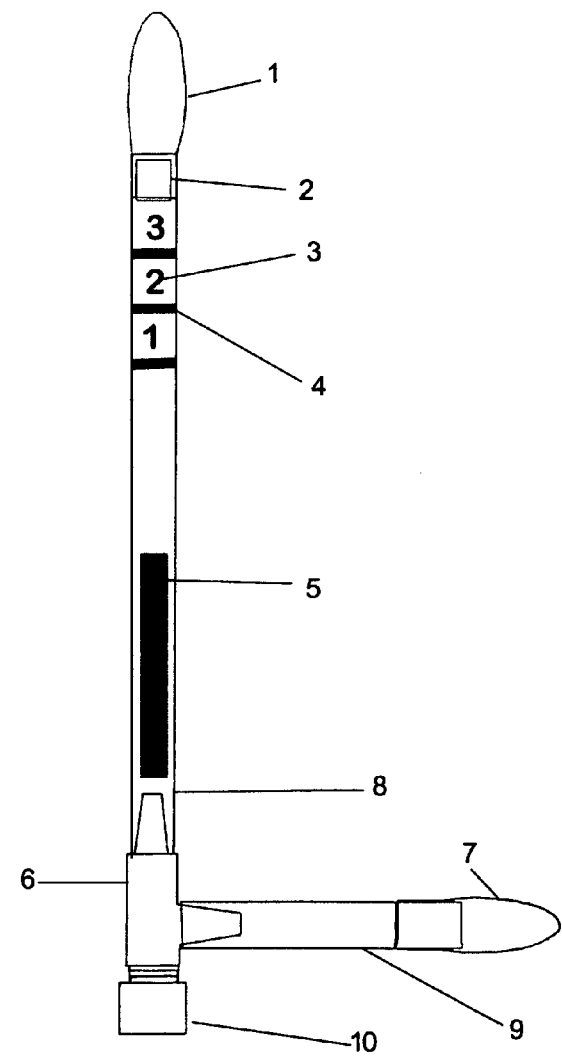
FIG. 5 depicts the L-shaped tongue exercise with control valve.

FIG. 5 illustrates the present invention in the L-shaped model, which comes with a plastic two-way control valve 6 for increasing or decreasing the resistance. This tongue exerciser is easier for some patients to see the feedback because it is at eye level. Pictured are two clear tubes 8 and 9 securely connected to the ports of the control valve 6. The interior diameter of the clear tubes 8 and 9 is 0.205" allowing the plastic control valve 6 ports with outer diameters of 0.2" to tightly fit inside the tube without the need to use an adhesive. The control valve's dial 10 turns to a fully open position. Inside the vertical clear tube 8 is the buoyant vial indicator 5 that rests inside the vertical tube 8. To prevent the vial indicator 5 from elevating out of the tube 8 into the expansion bulb 1 when the water is displaced by the tongue bulb's 7 compression, a hollow core plug 2 fits tightly into the vertical tube's 8 end. The graduations 4 and the numerical demarcations 3 are printed at the top of the vertical tube 8. The expansion bulb 1 fits tightly over the end of the vertical tube 8. The tongue bulb 7 fits securely over the horizontal tube 9. To fill the L-shaped unit with water, both bulbs 1 and 7 are removed. The horizontal tube 9 is placed under running water and filled. The tongue bulb 7 is filled with water and secured on to the horizontal tube 9. Then, the vertical tube 8 is placed under the running tap and is filled as the tongue bulb 7 is lightly squeezed. Once the vertical tube 8 is filled, the expansion bulb 1 is also filled with water and secured to the end of the vertical tube 8. The present invention is ready to be employed.

Figure 6:
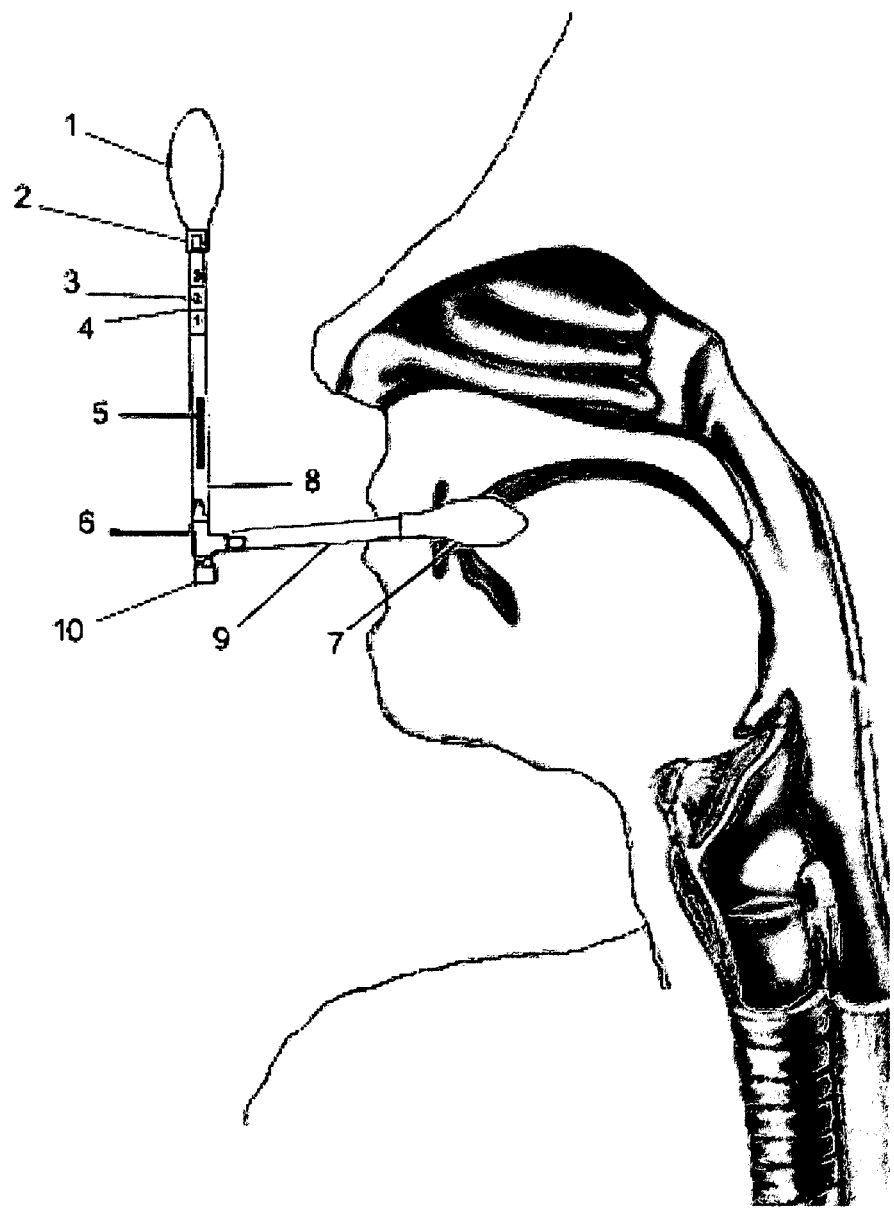
FIG. 6 depicts the L-shaped tongue exerciser with control valve in position for use.

FIG. 6 illustrates the device in position. The tongue bulb 7 is positioned on the patient's tongue and is pressed with as much force as possible. This compression displaces the water in the tubes 8 and 9 and raises the buoyant vial indicator 5 upward in the vertical tube 8. The user is able to view the height that the vial indicator raises by the graduations 4 and demarcations 3 as feedback to the strength of their effort. When the tongue releases the pressure against the tongue bulb 7, the vial indicator 5 descends to its resting position at the bottom of the vertical tube 8. This exercise is repeated 30× (or as prescribed by the clinician) 3× a day. The illustrations demonstrate the exercise devices and some of the possible alterations that can be made in the design.

I claim as deserving the protection of the United States Patent:

1. An exercise device for strengthening the tongue comprising:
    a first tube and a second tube, each of variable length;
    an adjustable two way pressure valve connecting first ends of the first and second tubes;
    the first tube being clear and having a buoyant colored vial indicator of incremental weight or length located therein;
    printed graduations and demarcations on the first tube;
    a hollow core plug inserted tightly into the second end of the first tube opposite the 2-way pressure valve to allow for fluid displacement there through while keeping the indicator within the first tube;
    a silicone tongue bulb attached to the second end of the second tube for tongue pressing against the hard palate;
    a silicone expansion bulb attached to the second end of the first tube which allows for fluid displacement; and
    the tubes, pressure valve, tongue bulb and expansion bulb creating a watertight capacity holding a fluid therein.

2. An exercise device as recited in claim 1, wherein the silicone expansion and tongue bulbs are detachable and have openings that have smaller interior diameters than the outer diameters of the clear tubes allowing the bulb's silicone lip to fit tightly over the tube ends to seal and yet allow for easy removal for filling the device with fluid.

3. An exercise device for strengthening the tongue as recited in claim 1,
    having a size and shape to be used with one hand such that hemiplegic patients can use the device without assistance and the threat of cross contamination.

4. An exercise device for strengthening the tongue as recited in claim 1,
    wherein the expansion bulb is positioned on opposing tube end to allow fluid displacement when the tongue bulb is compressed.

5. An exercise device for strengthening the tongue as recited in claim 1,
    wherein the silicone tongue bulb is capable of being placed on the dorsum of the tongue inside the mouth and compressed by the tip of the tongue's strength against the hard palate.

6. An exercise device for strengthening the tongue as recited in claim 1,
    wherein the buoyant vial indicator floats within the first tube and moves upward when the fluid is displaced by compression of the tongue bulb.

7. An exercise device for strengthening the tongue as recited in claim 1, wherein a difficulty or resistance of the exercise device can be adjusted by:
    modifying the weight or length of the buoyant vial indicator;
    by opening or closing the pressure valve;
    or by varying the length of at least one of the first and second tubes.

8. An exercise device for strengthening the tongue as recited in claim 1,
    wherein the tongue bulb and the expansion bulb are pressurized by fluid without electrical components.

9. An exercise device for strengthening the tongue as recited in claim 1,
    wherein the device is manufactured in plastic or a comparable material.

10. An exercise device for strengthening the tongue as recited in claim 1,
    wherein the expansion bulb and the tongue bulb can vary in size and configuration.

11. An exercise device for strengthening the tongue as recited in claim 1,
    wherein the tongue bulb is the only part of the device exposed to saliva reducing the parts in need of cleaning and at risk of contamination.

12. An exercise device as recited in claim 1, wherein specificity of movement is provided by the tongue moving in an upward movement toward the hard palate against the resistance of the tongue bulb thereby replicating the tongue's movement during the act of swallowing and speech, and strengthening of the tongue musculature occurs with consecutive repetition of the exercise to the point of muscle overload.

13. An exercise device for strengthening the tongue as recited in claim 1, wherein a feedback element demonstrates to a user, through the elevation of the vial indicator to the marked graduations, an amount of force that was used during the bulb compression.

14. An exercise device for strengthening the tongue as recited in claim 1,
    wherein the tongue bulb has a textured surface.

15. An exercise device for strengthening the tongue as recited in claim 1, wherein the graduations are calibrated for use as measurement.

16. An exercise device for strengthening the tongue comprising:
- a clear tube of variable length;
- a buoyant colored vial indicator of incremental weight or length located within the clear tube;
- printed graduations and demarcations on the clear tube;
- a hollow core plug inserted into each of first and second ends of the clear tube to allow for fluid displacement there through while keeping the indicator within the clear tube;
- a silicone tongue bulb attached to the first end of the clear tube for tongue pressing;
- a silicone expansion bulb attached to the second end of the clear tube which allows for fluid displacement;
- expansion and tongue bulb openings with smaller interior diameters than the outer diameter of the clear tube end to allow the silicone lips of the bulbs' orifices to fit tightly over the tube for sealing;
- tongue bulb and expansion bulb are removable to fill the device with fluid; and
- the tube, tongue bulb and expansion bulb creating a watertight capacity holding a fluid therein such that compression of the tongue bulb displaces the fluid, and thus the indicator, along the length of the tube.

* * * * *